(12) United States Patent
Le et al.

(10) Patent No.: US 7,891,234 B2
(45) Date of Patent: Feb. 22, 2011

(54) MULTI-SENSING DEVICE AND METHOD OF OPERATING

(75) Inventors: Kevin D. Le, Richland Hills, TX (US); Jeffrey J. Tooley, North Richland Hills, TX (US); Prabhakar B. Rao, Huntsville, AL (US)

(73) Assignee: Luraco Technologies, Inc., Arlington, TX (US)

( * ) Notice: Subject to any disclaimer, the term of this patent is extended or adjusted under 35 U.S.C. 154(b) by 229 days.

(21) Appl. No.: 12/247,301

(22) Filed: Oct. 8, 2008

(65) Prior Publication Data
US 2010/0083730 A1 Apr. 8, 2010

(51) Int. Cl.
G01N 15/08 (2006.01)
(52) U.S. Cl. .......................................................... 73/38
(58) Field of Classification Search .................... 73/38, 73/708; 210/90, 111
See application file for complete search history.

(56) References Cited
U.S. PATENT DOCUMENTS
5,702,592 A * 12/1997 Suri et al. ..................... 210/90

\* cited by examiner

Primary Examiner—Hezron Williams
Assistant Examiner—Tamiko D Bellamy
(74) Attorney, Agent, or Firm—Haynes and Boone, LLP

(57) ABSTRACT

A multi-sensing device is provided which includes a first sensor for sensing a temperature of the fluid flowing through the filter element, a second sensor for sensing a pressure generated by the fluid flowing through the filter element; and an indicator for indicating a condition of the filter system, and a microcontroller operatively coupled to the first and second sensors. The microcontroller executes instructions for receiving temperature data from the first sensor and pressure data from the second sensor; if the temperature data does not exceed a first temperature threshold, monitoring subsequent temperature data received from the first sensor until it exceeds the first temperature threshold; and if the temperature data exceeds the first temperature threshold: determining whether the temperature data exceeds a second temperature threshold and whether the pressure data exceeds a pressure threshold; if the temperature data exceeds the second temperature threshold, activating the indicator to indicate that the fluid is in an abnormal condition; and if the pressure data exceeds the pressure threshold, activating the indicator to indicate that the filter element is in a condemned condition.

25 Claims, 13 Drawing Sheets

Configuring MultiSENS Threshold Values

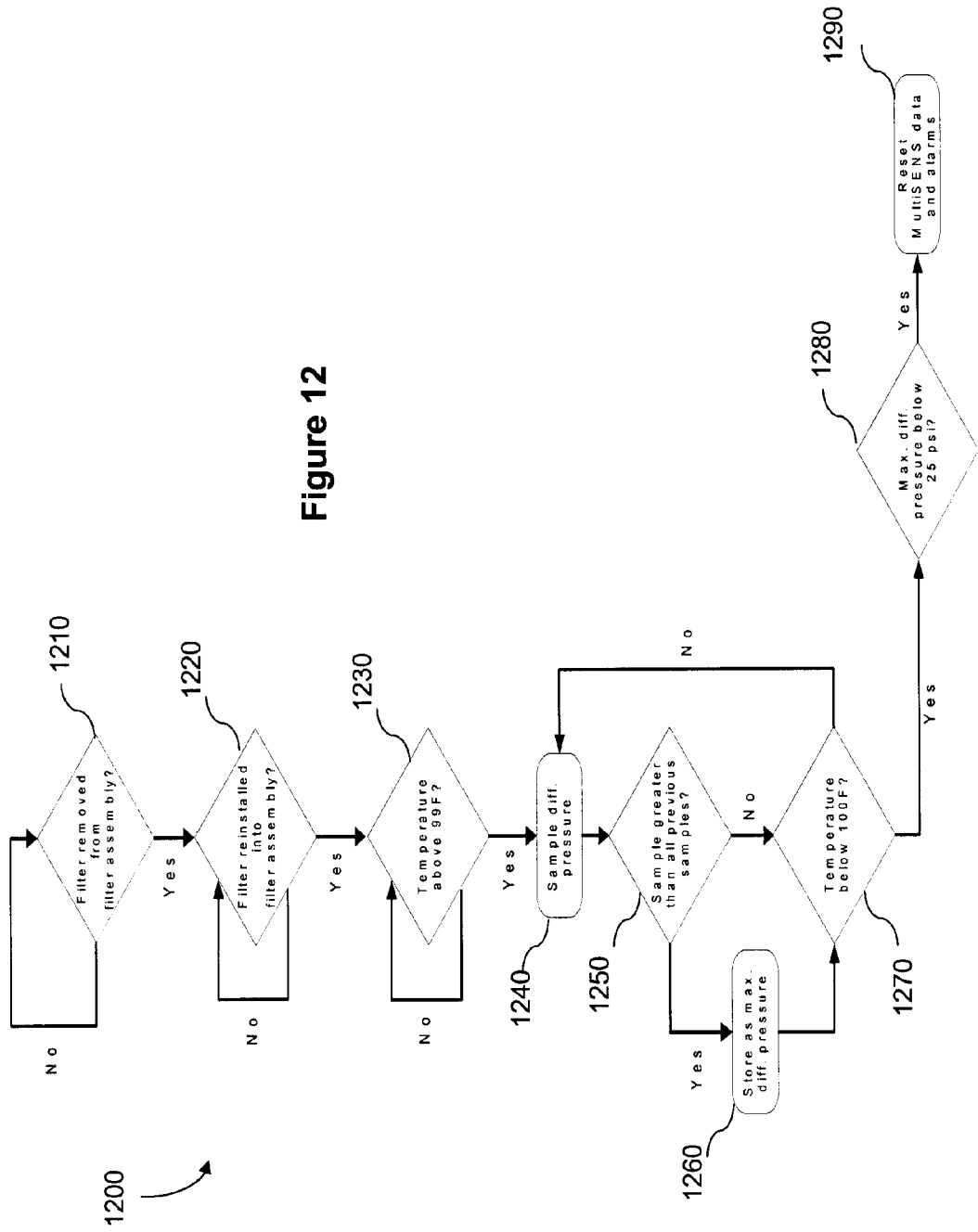

MULTI-SENSING DEVICE AND METHOD OF OPERATING

GOVERNMENT LICENSE RIGHTS

The U.S. Government has a paid-up license in this invention and the right in limited circumstances to require the patent owner to license others on reasonable terms as provided for by the terms of contract no. W911W6-08-C-0017 awarded by U.S. Army Research, Development, and Engineering Command (contract issued by Aviation Applied Technology Directorate).

BACKGROUND

Hydraulic systems are often used in various mechanical systems or electro-mechanical systems to actuate and/or control components of those systems. For example, in an aircraft system, a hydraulic system may use a fluid, such as oil, to actuate controllers, motors, gears, and other components of the aircraft system. As the fluid flows through the hydraulic system, the fluid may be contaminated with particles from various components of the aircraft system. The fluid needs to be filtered and cleaned so that the hydraulic system performs and operates properly. Accordingly, the hydraulic system typically employs a filter assembly that includes a filter element for filtering the fluid. Over time, the filter element may become condemned or contaminated. In some circumstances, the condemned filter element can adversely affect the flow of the fluid (e.g., pressure) in the hydraulic system thereby degrading the performance of the hydraulic system and causing components of the aircraft system to operate improperly. Thus, it is important to accurately monitor and detect when the filter element and/or the fluid in the hydraulic system requires changing.

Therefore, what is needed is a new and improved multi-sensing device for sensing characteristics of a fluid flowing through a filter element in a fluid system.

SUMMARY

A multi-sensing device for sensing a plurality of characteristics of a fluid flowing through a filter element in a fluid system is provided. The multi-sensing device includes a first sensor for sensing a temperature of the fluid flowing through the filter element, a second sensor for sensing a pressure generated by the fluid flowing through the filter element, a third sensor for sensing a quality of the fluid flowing through the filter element, an indicator for indicating a condition of the fluid system, and a microcontroller operatively coupled to the first, second, and third sensors. The microcontroller executes instructions for receiving temperature data from the first sensor, pressure data from the second sensor, fluid quality data from the third sensor; if the temperature data does not exceed a first temperature threshold, monitoring subsequent temperature data received from the first sensor until it exceeds the first temperature threshold; if the temperature data exceeds the first temperature threshold: determining whether the temperature data exceeds a second temperature threshold, whether the pressure data exceeds a pressure threshold, or whether the quality data exceeds a fluid quality threshold; if the temperature data exceeds the second temperature threshold, activating the indicator to indicate that the fluid is in an abnormal condition; and if the pressure data exceeds the pressure threshold, activating the indicator to indicate that the filter element is in a condemned condition; and if the fluid quality data exceeds the fluid quality threshold, activating the indicator to indicate that the fluid is contaminated.

A method is provided for operating a multi-sensing device that senses a plurality of characteristics of a fluid flowing through a filter element in a fluid system. The method includes acquiring data from a first sensor and a second sensor of the multi-sensing device, the first sensor for sensing a temperature of the fluid flowing through the filter element and the second sensor for sensing a pressure generated by the fluid flowing through the filter element; if the temperature data does not exceed a first temperature threshold, monitoring subsequent temperature data acquired from the first sensor until it exceeds the first temperature threshold; and if the temperature data exceeds the first temperature threshold: determining whether the temperature data exceeds a second temperature threshold and whether the pressure data exceeds a pressure threshold; if the temperature data does not exceed the second temperature threshold, evaluating subsequent temperature data acquired from the first sensor to determine whether it exceeds the second temperature threshold; if the temperature data exceeds the second temperature threshold, activating an indicator to indicate that the fluid is in an abnormal condition; if pressure data does not exceed the pressure threshold, evaluating subsequent pressure data acquired from the second sensor to determine whether it exceeds the pressure threshold; and if the pressure data exceeds the pressure threshold, activating the indicator to indicate that the filter element is in a condemned condition.

A fluid system is provided which includes a filter assembly having an inlet port and an outlet port, the filter assembly including a filter element for filtering the fluid flowing in the inlet port and out the outlet port, a multi-sensing device operatively coupled to the filter assembly for sensing a plurality of characteristics of the fluid flowing through the filter element of the filter assembly. The multi-sensing device includes a first sensor for sensing a temperature of the fluid, a second sensor for sensing a pressure generated by the fluid flow, a third sensor for sensing a quality of the fluid, an indicator for indicating a condition of the fluid element and the fluid, memory for storing data, and a microcontroller having instructions for: acquiring temperature data from the first sensor, pressure data from the second sensor, and fluid quality data from the third sensor; and if the temperature data exceeds a first temperature threshold: determining whether the temperature data exceeds a second temperature threshold, whether the pressure data exceeds a pressure threshold, or whether the fluid quality data exceeds a fluid quality threshold; if the temperature data exceeds the second temperature threshold, activating the indicator to indicate that the fluid is in an abnormal condition and storing the temperature data in the memory; if the pressure data exceeds the pressure threshold, activating the indicator to indicate that the filter element is in a condemned condition and storing the pressure data in memory; and if the fluid quality data exceeds the fluid quality threshold, activating the indicator to indicate that the fluid is contaminated.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. Furthermore, all features may not be shown in all drawings for simplicity.

FIG. 12 is a flowchart depicting a method for operation of the multi-sensing device of FIG. 3 during a filter element change.

DETAILED DESCRIPTION

Figure 1:
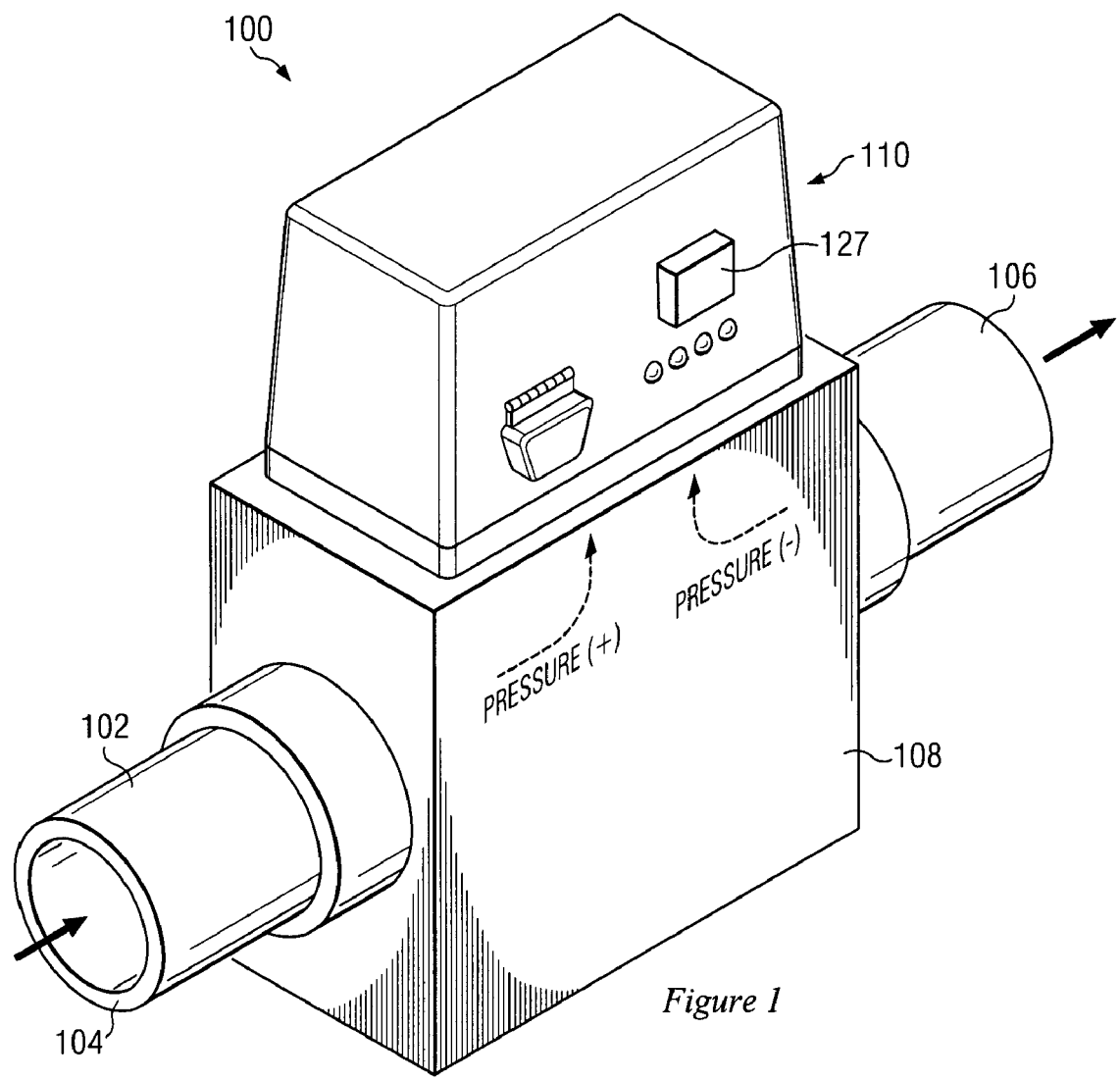
FIG. 1 is a diagrammatic representation depicting a portion of a hydraulic system in which embodiments disclosed herein may be implemented.

The present invention relates generally to checking parameters associated with components in a hydraulic system. It is understood, however, that the following disclosure provides many different embodiments, or examples, for implementing different features of the invention. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Referring to FIG. 1, illustrated is a diagrammatic representation of a portion of a hydraulic system 100 in which embodiments disclosed herein may be implemented. The system 100 includes a hydraulic line 102 with an inlet port 104 and an outlet port 106. A hydraulic fluid, for example oil, flows into the inlet port 104, through a filter assembly 108, and then out of the outlet port 106. The filter assembly 108 is coupled to the hydraulic line 102 and includes a filter element that filters the hydraulic fluid as it flows through the hydraulic line 102. Also, the filter assembly 108 includes an opening for receiving a multi-sensing assembly 110. The multi-sensing assembly 110 includes an extended portion that fits into the filter assembly 108 in such a manner that a sensing portion of the multi-sensing assembly 110 contacts the hydraulic fluid as it flows through the filter assembly 108 as will be discussed in detail later. Accordingly, the multi-sensing assembly 110 is capable of sensing and monitoring various characteristics of the hydraulic fluid as it flows through the filter assembly 108. The various characteristics of the hydraulic fluid can be used to provide a contamination/condemnation status of the filter element and hydraulic fluid in the filter assembly 108. It is understood that the hydraulic system 100 may be utilized to actuate and/or control components of various machines, mechanical systems, electro-mechanical systems, or other suitable systems. Thus, it is important to monitor and detect the contamination/condemnation status of the filter element and fluid in the filter assembly 108 so that the hydraulic system 100 is properly operating for its intended purpose.

Figure 2A:
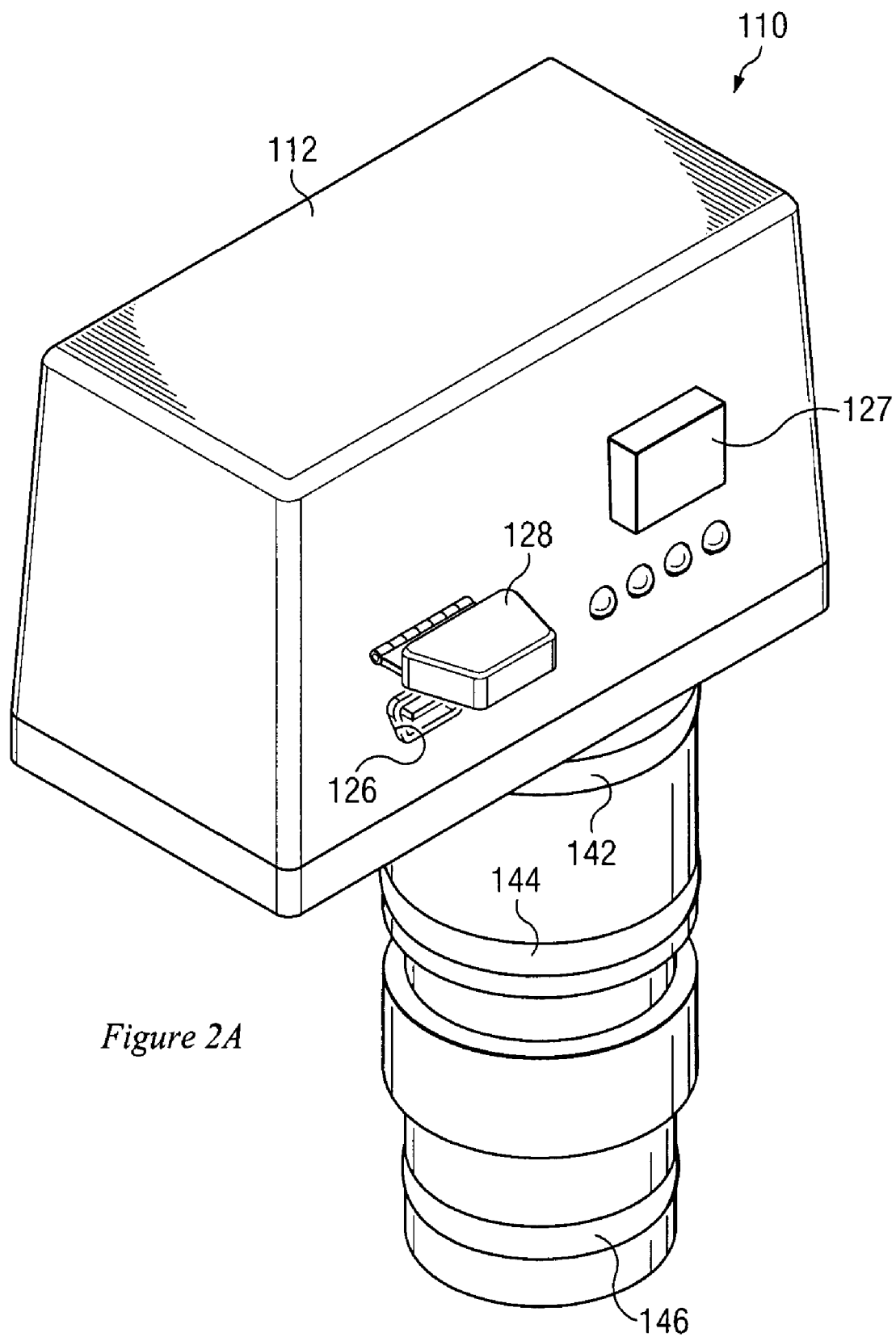
FIGS. 2A and 2B are diagrammatic representations depicting a multi-sensing assembly that may be implemented in the portion of the hydraulic system of FIG. 1.
Figure 2B:
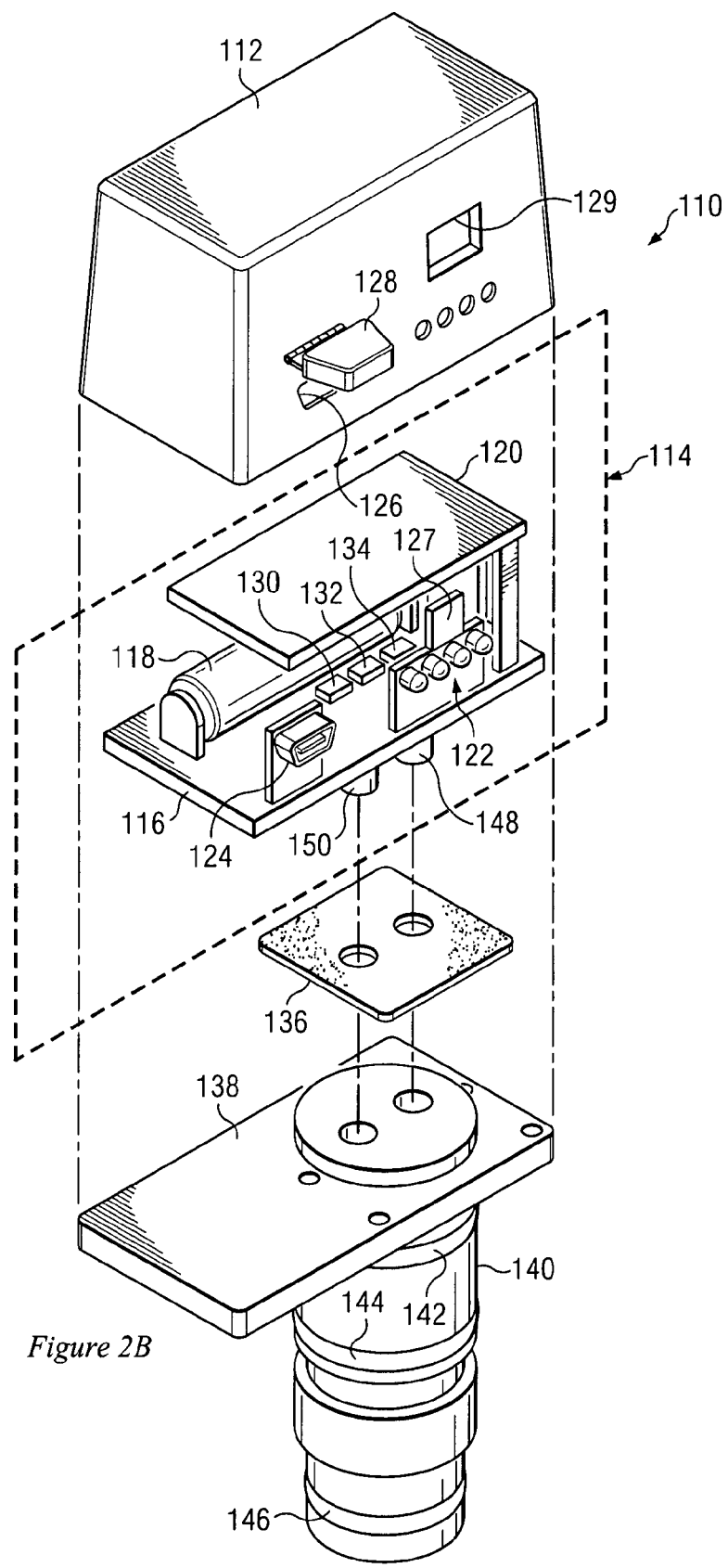

Referring to FIGS. 2A and 2B, illustrated are diagrammatic representations of the multi-sensing assembly 110 that may be implemented in the hydraulic system 100 of FIG. 1. FIG. 2B is an exploded view of the multi-sensing assembly 110. The multi-sensing assembly 110 includes a top housing 112 that provides a casing for a multi-sensing device 114. The multi-sensing device 114 senses and monitors various characteristics of the hydraulic fluid as it passes through the filter assembly and the filter element 108. In the present embodiment, the multi-sensing device 114 includes a printed circuit board (PCB) 116. The multi-sensing device 114 includes a rechargeable battery 118 that is coupled to the PCB 116. The battery 118 provides power to the various components of the multi-sensing device 114. The multi-sensing device 114 further includes an energy harvesting circuit 120, for example a vibration energy harvesting circuit, that is coupled to the PCB 116. The energy harvesting circuit 120 may harvest vibration energy and convert it into electrical energy for recharging the battery 118.

The multi-sensing device 114 also includes a plurality of status light-emitting-diodes (LEDs) 122 on the PCB 116. For example, the status LEDs 122 may include one of a pressure status LED, a temperature status LED, a fluid quality status LED, a battery status LED, and a data status LED. A blinking pressure status LED indicates that the multi-sensing device 114 is in a calibration mode of operation. A blinking pressure status LED, temperature status LED, or fluid quality LED indicates that a parameter of hydraulic system 100 is outside a preferred or a safe range of operation. Moreover, the data status LED is turned on to indicate that a data extraction application is in preparation to communicate with or is in communication with the multi-sensing device 114. It is understood that the number of status LEDs and the functionality of the status LEDs may vary depending on the particular application that the multi-sensing device 114 is used for.

The multi-sensing device 114 further includes a data communication port 124, for example a universal serial bus (USB) port, that allows the multi-sensing device 114 to connect to a computing device, such as a PC, laptop computer, personal digital assistant (PDA) or other suitable device, for calibration, diagnostic, maintenance, or other suitable purposes. Alternatively, the data communication port 124 may optionally be configured for other types of data communication interfaces as is known in the art. The computing device connects to the data communication port 124 through a data communication port opening 126 in the top housing 112. Moreover, the top housing 112 includes a data communication port cover 128 that protects the data communication port 124 from undesirable elements.

Further, the multi-sensing device 114 includes a wake/calibrate button 127 that is coupled to the PCB 116. The wake/calibrate button 127 is used to wake and calibrate the multi-sensing device 114. The top housing 112 has an opening 129 for the wake/calibrate button 127. The wake/calibrate button 127 protrudes through the opening 129 so that it can be depressed and activated by a user external to the multi-sensing device 114.

In addition, the multi-sensing device 114 includes a temperature sensor circuit 130, a pressure sensor circuit 132, and a fluid contamination sensor circuit 134. The sensor circuits 130, 132, and 134 are coupled to the PCB 116 and provide the multi-sensing device 114 with multi-sensing functionality.

For example, the temperature sensor circuit 130 senses a temperature of the hydraulic fluid passing through the filter assembly 108. The pressure sensor circuit 132, for example, senses a differential pressure across the filter assembly 108. Moreover, the fluid contamination sensor circuit 134, for example, includes an optical absorption sensor circuit. The fluid contamination sensor circuit 134 senses an optical absorption of the hydraulic fluid that allows for a determination of various characteristics of the hydraulic fluid quality. For example, an optical absorption spectrum of the hydraulic fluid may be analyzed to determine the fluid quality. Hydraulic fluid that is clean exhibits an optical absorption structure that is different than hydraulic fluid that is contaminated. The optical absorption sensor may use a narrow wavelength bandwidth (e.g., infrared region) to detect when the fluid is contaminated. Further, the unique absorption signature of the hydraulic fluid may be analyzed to determine the fluid quality, such as, metallic particulate content, viscosity, water content, acidity, and oxidation. Alternatively, the fluid contamination sensor circuit 134 may optionally utilize other types of sensors such as a dielectric sensor or water-content sensor for sensing the fluid quality.

The multi-sensing assembly 110 further includes a gasket 136 and a filter assembly interface 138. The gasket 136 provides a sealant between the filter assembly interface 138 and the multi-sensing device 114. The multi-sensing assembly 110 also includes a tubular extension 140 that fits into the filter assembly 108. The tubular extension 140 includes hydraulic fluid sealing rings 142, 144, and 146. The hydraulic fluid sealing rings 142, 144, and 146 provide a sealant between the tubular extension 140 and the hydraulic fluid in the filter assembly 108. The multi-sensing device 114 further includes ports 148 and 150 that protrude through the gasket 136, the filter assembly interface 138, and the tubular extension 140. The ports 148 and 150 protrude into the hydraulic fluid in the filter assembly 108. The hydraulic fluid is directed through the ports 148 and 150 to the sensing elements of the temperature sensor circuit 130, the pressure sensor circuit 132, and the fluid contamination sensor circuit 134.

Figure 3:
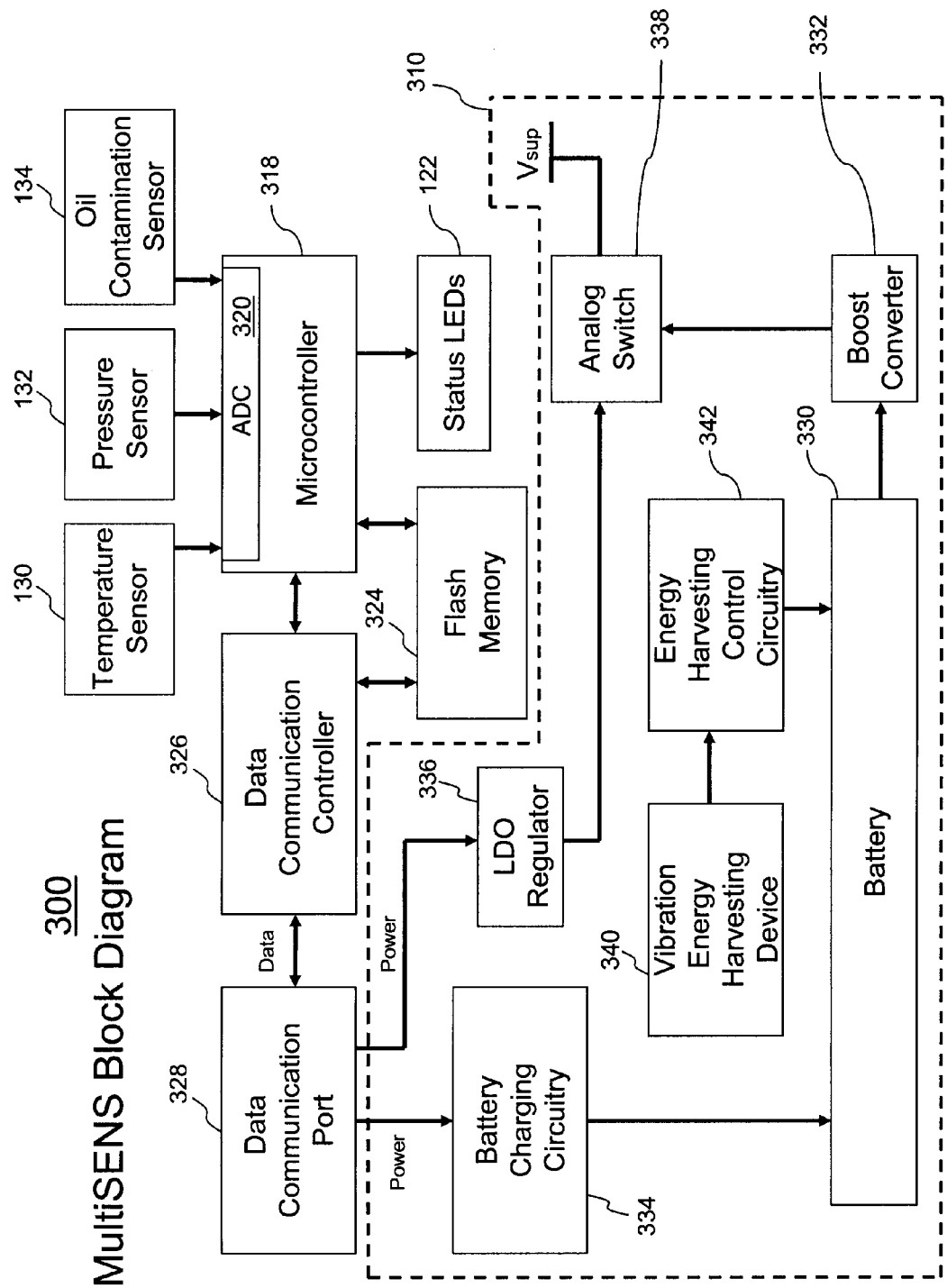
FIG. 3 is a block diagram depicting a hardware configuration of a multi-sensing device that may be implemented in the multi-sensing assembly of FIGS. 2A and 2B.

Referring to FIG. 3, illustrated is a block diagram 300 of a hardware configuration of the multi-sensing device 114 that may be implemented in multi-sensing assembly 108 of FIGS. 2A and 2B. Similar features in FIGS. 2 and 3 are numbered the same for clarity. The block diagram 300 includes the temperature sensor circuit 130, the pressure sensor circuit 132, and the fluid contamination sensor circuit 134. The sensor circuits 130, 132, and 134 are coupled to a processing device, such as microcontroller 318. The microcontroller 318 is the central processing unit in the hardware configuration of the multi-sensing device 114. The microcontroller 318 includes an internal analog-to-digital converter (ADC) 320. In an alternative embodiment, the ADC 320 may optionally be external to the microcontroller 318. In that case, the external ADC is coupled to the microcontroller 318. The ADC 320 receives signals from the sensors circuits 130, 132, and 134 and converts these analog signals into digital signals that are processed and managed by the microcontroller 318. The microcontroller 318 is further coupled to the status LEDs 122 for controlling and activating the status LEDs.

The block diagram 300 of the multi-sensing device 114 includes memory, for example a flash memory 324. The flash memory 324 is coupled to the microcontroller device 318. In an alternative embodiment, the flash memory 324 is integrated into the microcontroller device 318. Furthermore, the flash memory 324 is coupled to a data communication controller 326. The flash memory 324 stores various threshold values, for example a temperature threshold, a differential pressure threshold, a fluid quality threshold, and a threshold for elapsed time since a calibration of the multi-sensing device 114 was activated. The threshold values may be programmed initially and later re-programmed by a user using a data extraction application that engages with the multi-sensing device 114. It is understood the other threshold values may be provided as default or pre-defined threshold values that are specified by the manufacturer for a particular hydraulic system or for a particular type of hydraulic fluid.

The data communication controller 326 is coupled to the microcontroller 318 and provides control and management of a data communication port 328. The data communication port 328 and communication controller 326 is in conformance with, for example, the universal serial bus (USB) communication protocol. In alternative embodiments, the data communication port 328 and communication controller 326 enables other communication protocols as is known in the art. The data communication port 328 may connect to a diagnostic or computing device, such as a PC, so that data may be uploaded from the multi-sensing device 114 from the flash memory 324 to the PC for diagnostic and/or maintenance purposes. To that extent, the PC includes the data extraction application. Moreover, the data extraction application further allows a user to set threshold values and re-program firmware into the flash memory 324 via the data communication port 328. Accordingly, this allows the multi-sensing device 114 to be customized by the user for their particular fluid system.

In addition, the block diagram 300 of the multi-sensing device 114 also includes a power supply 310 that provides power to the multi-sensing device 114. For example, the power supply 310 includes a battery 330 (such as the rechargeable battery 118 of FIG. 2B) that provides power to the multi-sensing device 114. The battery 330 is coupled to a boost converter circuit 332 that boosts the battery voltage to a desired level for use in powering the multi-sensing device 114. The power supply 310 further includes a battery charging circuit 334 that charges the battery 330. For example, the battery charging circuit 334 may use the power provided by the data communication port 328 to charge the battery 330. In addition, the power provided by the data communication port 328 may also be directed to a voltage regulator, such as a low dropout regulator (LDO) 336. The LDO 336 is coupled to an analog switch 338. Also, the boost converter 332 is coupled to the analog switch 338. The analog switch 338 may be selected to use power from the boost converter 332 or the LDO 336 to power the multi-sensing device 114.

In one embodiment, the energy harvesting circuit 120 includes an energy harvesting device 340 and an energy harvesting control circuit 342 to provide power to the multi-sensing device 114. Accordingly, the multi-sensing assembly 110 may generate its own power, independent from power provided by a machine, such as an aircraft, in which the multi-sensing assembly 110 resides. Moreover, the energy harvesting device 340 and the energy harvesting control circuit 342 provide power to the multi-sensing device 114 without dependence on the battery 330 and therefore, use of the energy harvesting device 340 and the energy harvesting control circuit 342 may prevent depletion of battery 330 while the multi-sensing device 114 is in use. In one embodiment, the energy harvesting device 340 includes a vibration energy harvesting device that translates energy from ambient vibrations into electrical energy. Alternatively, the energy harvesting device 340 may include a heat or light energy harvesting device that translates energy from ambient heat or light into electrical energy. The multi-sensing assembly 110 is used in a hydraulic system of an aircraft that exhibits vibration energy in the regime of 5 to 50 Hz and therefore, the energy harvesting device 340 is specified to work in this range. In an alternative embodiment, a machine, such as an aircraft, in which the multi-sensing assembly 110 resides, supplies power to the multi-sensing device 114. Further, the multi-sensing device 114 may be powered by any suitable low voltage system.

Figure 4:
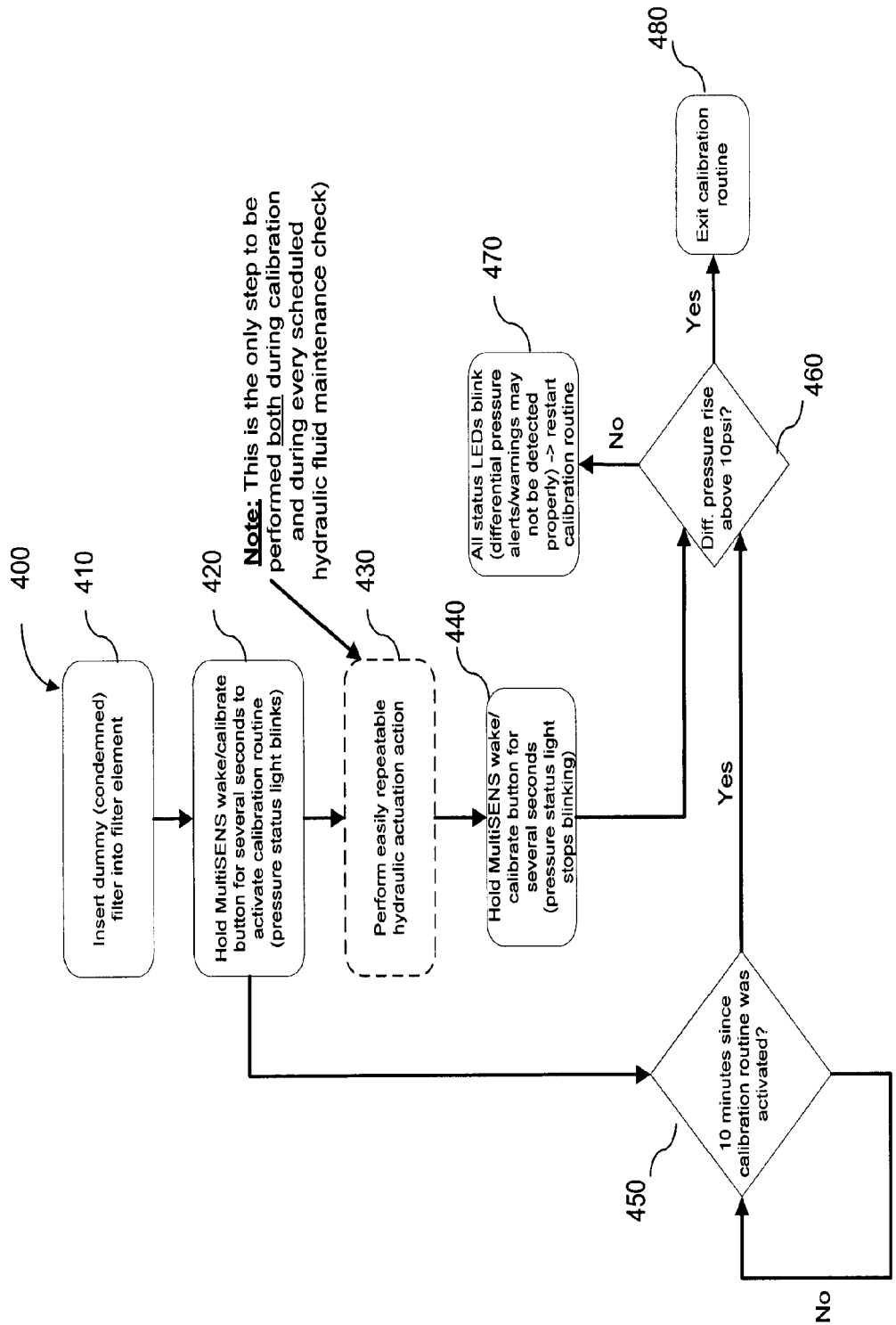
FIG. 4 is a flowchart depicting a method for calibrating the multi-sensing device of FIG. 3.

Referring also to FIG. 4, illustrated is a flowchart of a method 400 for calibrating the multi-sensing device 114. The calibration procedure 400 enables the multi-sensing device 114 to capture a differential pressure that is generated across a dummy filter element, thereby emulating a condemned filter element state in response to a known, easily repeatable hydraulic actuation action that a maintenance technician performs. The measured differential pressure correlates to a flow rate of the hydraulic fluid flowing through the condemned filter element state. Accordingly, the measured differential pressure provides a basis for automatically calculating a pressure alert threshold and a pressure warning threshold for the multi-sensing device 114. For example, the alert threshold may be set to 60% of the measured differential pressure, while the warning threshold may be set to 80% of the measured differential pressure. The specific percentages may vary depending on design requirements of a particular hydraulic system. To enhance the reliability of the multi-sensing device 114 for determining when the hydraulic fluid and/or filter element is near (e.g., alert threshold) or at (e.g., warning threshold) a point of requiring changing, a maintenance routine should include performing the same hydraulic actuation that was performed during calibration as part of scheduled hydraulic fluid maintenance checks. Accordingly, a differential pressure measured across the filter element during the maintenance routine may be compared to the pressure alert threshold and pressure warning threshold to accurately and reliably determine the condition of the filter element.

The calibration procedure 400 should be performed immediately after the multi-sensing assembly 110 is installed in the hydraulic system 100, and periodically thereafter, for example every one to two years or other suitable time period, to ensure that condemnation of the filter element continues to be accurately detected. If the calibration procedure 400 is not performed, or if the multi-sensing device 114 has been set to ignore the calibration derived thresholds, then the multi-sensing device 114 may use the threshold values that are programmed in the memory as the alert threshold level and warning threshold level. For example, the threshold values may include default threshold values provided by a maintenance technician or other user of the multi-sensing device, the default threshold values depending on requirements of a particular hydraulic system and/or hydraulic fluid.

The calibration procedure 400 begins in block 410 where a dummy filter is inserted into the filter assembly 108. The dummy filter emulates a condemned hydraulic filter element in the filter assembly 108. The calibration procedure 400 continues in block 420, where the wake/calibrate button 127 is depressed and held for several seconds to activate the calibration routine. One of the status LEDs 122 is a pressure status LED. The pressure status LED begins to blink once the multi-sensing device 114 has entered the calibration mode of operation. For example, the blinking exhibits a period of about two seconds and a duty cycle of about 50%. The calibration procedure 400 proceeds to block 430, where a maintenance technician performs an easily repeatable hydraulic actuation action. For example, the hydraulic actuation action should be performed during regularly scheduled hydraulic oil maintenance checks. Then, in block 440, the wake/calibrate button is held for several seconds once again. This will stop the pressure status LED from blinking and will turn off the pressure status LED, indicating that the multi-sensing device 114 is ready to prepare for exiting the calibration mode of operation.

The calibration procedure 400 continues to block 450, where the calibration routine determines how much time has elapsed since the calibration routine was activated. In other words, how much time has elapsed since the maintenance technician depressed and held the wake/calibrate button for several seconds (block 420). If the elapsed time since calibration activation exceeds a predetermined threshold value, the multi-sensing device 114 prepares to exit the calibration routine and the pressure status LED stops blinking and turns off. In one example, the predetermined elapsed time threshold value is set to ten minutes. During the calibration procedure 400, the calibration routine will check to determine if ten minutes or more has elapsed since the calibration mode of operation was activated. If ten minutes or more has elapsed since activation of the calibration routine, the multi-sensing device 114 automatically prepares to exit the calibration mode of operation, and the pressure status LED automatically turns off.

In preparation for exiting the calibration routine, in block 460, the multi-sensing device 114 determines whether the differential pressure has risen above a predetermined value. For example, in one embodiment, the predetermined value is 10 psi. If the differential pressure does not rise above the predetermined value, the calibration procedure 400 proceeds to block 470 where for example, the status LEDs 122 start blinking to indicate that the calibration routine was not performed successfully. This informs the maintenance technician that the calibration routine must be performed again. If the differential does rise above the predetermined value, the calibration procedure 400 proceeds to block 480, where the calibration routine is exited and the calibration procedure is complete.

Figure 5:
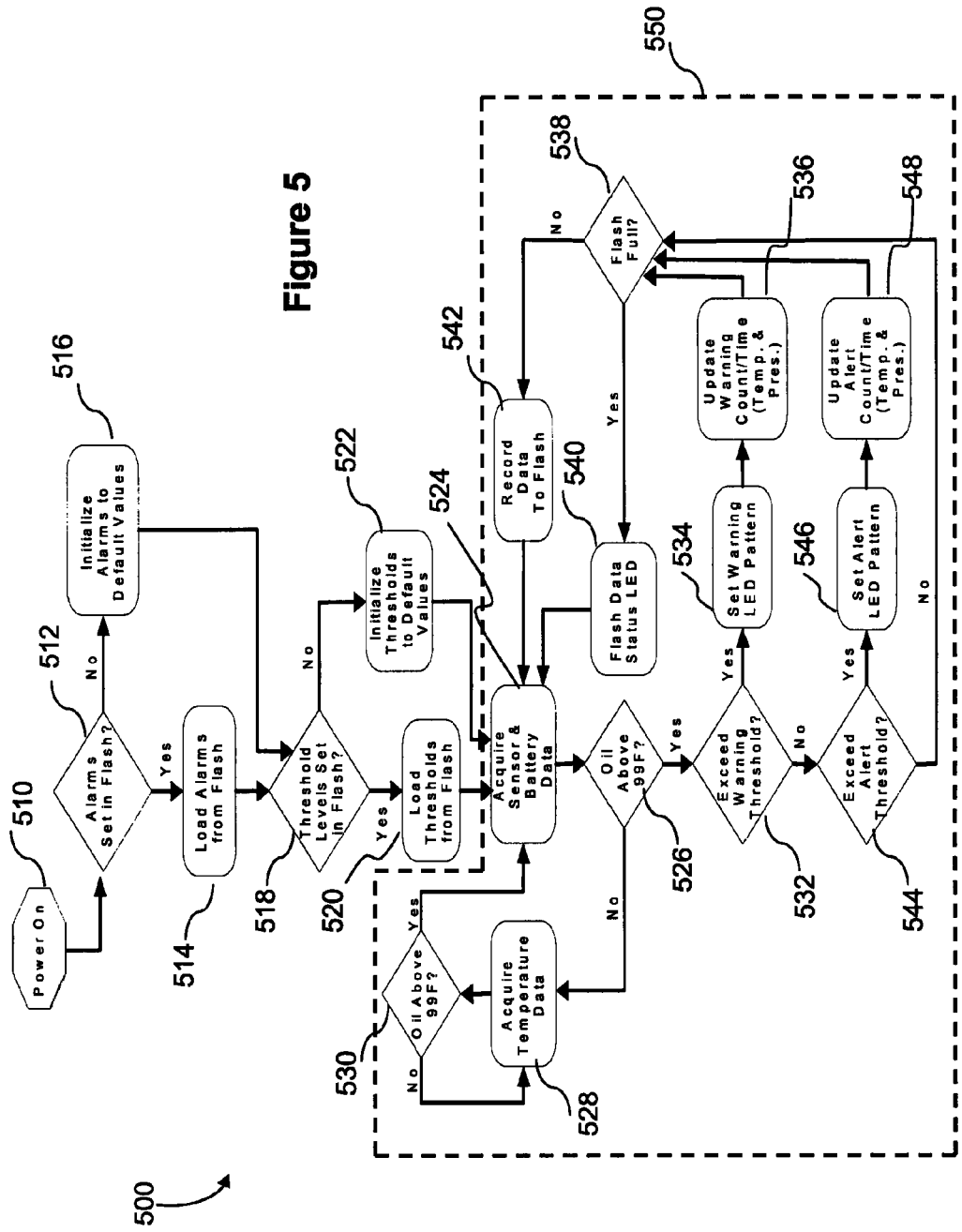
FIG. 5 is a flowchart depicting a method for normal operation of the multi-sensing device of FIG. 3.

Referring also to FIG. 5, illustrated is a flowchart of a method 500 for normal operation of the multi-sensing device 114 in accordance with an embodiment. The method 500 begins in block 510 where the multi-sensing device 114 is powered on. In one embodiment, the multi-sensing device 114 powers on when it is inserted into the filter assembly 108, or when a data port cable supplies power to the multi-sensing device 114 after either the multi-sensing device has been removed from the filter assembly 108 or the battery 330 has been completely drained due to extended inactivity. Power for the multi-sensing device 114 may be provided by various types of power sources. For example, the multi-sensing device 114 may be powered by the battery 330, the energy harvesting device 340 and the energy harvesting control circuit 342, or power provided by the aircraft or machine in which the hydraulic system 100 resides.

The method 500 continues in block 512 where it is determined whether there are any alarms stored in the flash memory 324. For example, if the multi-sensing device 114 has been inactive for an extended period of time, the current drawn by the multi-sensing device 114 may fully drain the battery 330. If it is determined that alarms are set in the flash memory 324, the method 500 continues to block 514 where the alarms are loaded into the microcontroller 318 for use in the main processing loop 550 and the status LEDs 122 (e.g., temperature status LED, pressure status LED, fluid quality status LED, battery status LED, and data status LED) changed in accordance with the stored alarm states. However, if there are no alarms set in the flash memory 324, the method 500 continues to block 516 where the default alarm states are loaded into the microcontroller 318 for use in the main processing loop 550. For example, the default alarm states include no alarms.

The method 500 continues to block 518 where the flash memory 324 is checked to determine if threshold levels have been stored in the memory. For example, the threshold levels may be stored in the flash memory 324 by a user programming these values. If it is determined that threshold levels are found in the flash memory 324, the method 500 continues to block 520 where the threshold levels are loaded from the flash memory 324 into the microcontroller 318 for use in the main processing loop 550. If it is determined that the threshold levels are not stored in the flash memory 324, the method 500 continues to block 522 where default threshold levels are loaded into the microcontroller 318 for use in the main processing loop 550. In the present embodiment, the threshold levels may include a temperature threshold levels, a differential pressure threshold level, a fluid quality threshold level, or other threshold levels.

The method 500 continues in block 524 where the multi-sensing device 114 enters a loop of continuously acquiring and storing sensor data and battery data. For example, the sensor data includes temperature data from the temperature sensor circuit 130, pressure data from the pressure sensor circuit 132, and fluid quality data from the fluid contamination sensor circuit 134 of FIG. 3. In one embodiment, the sensor data and battery data acquisition loop is operable when the temperature of the hydraulic fluid is above a predetermined value. This ensures that the hydraulic fluid has been flowing in the hydraulic system 100 for a sufficient amount of time such that the collected data is valid and proper. That is, the hydraulic fluid has been flowing in the hydraulic system 100 under operating conditions for a sufficient period of time. In one embodiment, a predetermined value of 99° F. is loaded into the microcontroller 318 for use in the main processing loop 550. The predetermined value is loaded from the user programmed threshold levels in the flash memory 324 (block 518) or from the default threshold levels stored in the flash memory 324 (block 522).

For example, when the hydraulic fluid temperature is above the predetermined threshold value, a sampling frequency is approximately 100 Hz. In this case, every 25 samples are averaged so that the multi-sensing device 114 determines the sensor status and battery status approximately every 0.25 seconds. In one embodiment, the hydraulic fluid temperature is assumed to meet the minimum temperature criteria the first time through the sensor data and battery data acquisition loop. The method 500 continues to block 526 where it is determined whether the hydraulic fluid temperature is above the predetermined value of 99° F. If not, the method 500 proceeds to block 528 where temperature data is acquired, for example every 30 seconds, and continues to acquire temperature data until the fluid temperature is above 99° F. The method 500 continues to block 530 where it is determined whether the hydraulic fluid temperature is above 99° F. If the fluid temperature falls below the predetermined threshold value, then the method 500 loops back to block 528 and continues to acquire temperature data periodically, for example every 30 seconds, until the hydraulic fluid temperature is above the predetermined threshold value of 99° F.

If the hydraulic fluid temperature is above the predetermined threshold value of 99° F., the method 500 loops back to block 524 to perform status checking. For example, status checking includes acquiring and storing sensor data (e.g., temperature data, pressure data, and fluid quality data) and battery data to determine whether any warning or alert thresholds have been exceeded. It is understood that the warning and alert thresholds are automatically calculated for each of the temperature threshold, pressure threshold, and fluid quality threshold stored in memory. As discussed above, in block 526 it is determined whether the hydraulic fluid temperature is above the predetermined threshold value. If yes, the method 500 continues to block 532 where it is determined whether any of the sensor data and battery data exceed the predetermined warning thresholds. These warning threshold levels may be loaded from the flash memory 324 as discussed above with respect to block 520 or initialized to default values as discussed in block 522.

The sensor data are provided by each of the sensing modalities (e.g., temperature sensor circuit 130, pressure sensor circuit 132, and fluid contamination sensor circuit 134). The sensor data (e.g., temperature, pressure, and fluid quality data) includes an average of a group of 25 samples. If the averaged sensor data from any one of the sensing modalities exceeds its corresponding warning threshold, the method 500 continues to block 534. It should be noted that the warning threshold for the pressure data corresponds to a potentially condemned condition of the filter element (e.g., blockage due to a condemned filter element), the warning threshold (different from the predetermined threshold discussed above) for the temperature data corresponds to a potential problem in the hydraulic system (e.g., overheating of the fluid), and the warning threshold for the fluid quality data corresponds to a potential problem with the hydraulic fluid (e.g., contamination of the oil). In block 534, one of the status LEDs 122 is a warning LED that is activated to blink periodically. For example, the warning LED blinks within a period of not more than one second and a duty cycle of not more than 20%. It is understood that the blinking warning LED corresponds to one or more of the temperature status LED, pressure status LED, fluid quality status LED, and battery status LED and depends on which data exceeded its corresponding warning threshold. If the sensing modality is temperature or pressure, the method 500 continues to block 536 where its warning count/time is also updated. The warning count/time corresponds to the number of times and total time the collected temperature and pressure data have exceeded the corresponding warning and alert thresholds. This information may confirm the reliability and proper operation of the multi-sensing device to accurately detect potential problems of the hydraulic system.

The method 500 continues to block 538 in preparation to record the sensor data into the flash memory 324. In block 538, it is determined whether the flash memory 324 is full. If the flash memory 324 is full, the method 500 continues to block 540 where the warning LED continues to blink rapidly until the sensor data and status is reset. Accordingly, this will ensure that a maintenance technician or other user of the multi-sensing device takes appropriate action such as extracting the stored data and erasing the data to free-up memory for further operation. If the flash memory 324 is not full, the method 500 proceeds to block 542 where the sensor data are recorded into the flash memory 324. After recording the data, the method 500 loops back to block 524 in the main processing loop 550.

If the sensor data (from the sensing modalities) does not exceed its corresponding warning threshold as determined in block 532, the method 500 continues to block 544 where it is determined whether the sensor data exceeds its corresponding predetermined alert threshold. If yes (which means that the sensor data is between the warning threshold and the alert threshold), the method 500 continues to block 546 where the warning LED is activated to blink periodically. For example, the warning LED blinks with a period of no more than ten seconds and a duty cycle of no more than 20%. It should be noted that the blinking of the warning LED in the warning condition (e.g., the sensor data exceeds the warning threshold) may be faster than the blinking of the warning LED in the alert condition so that a maintenance technician or other user of the multi-sensing device can differentiate between the two conditions and can take appropriate and/or remedial action. It should also be noted that the alert threshold corresponds to a less severe condition as compared to the warning threshold. That is, the alert threshold indicates that the sensor data is near a potential problem discussed above and that some component of the hydraulic system may require further evaluation. If the sensing modality is temperature or pressure, the method 500 continues to block 548 where its alert count/time is also updated. The alert count/time corresponds to the number of times and total time the collected temperature and pressure data has exceeded the corresponding warning and alert thresholds. This information may confirm the reliability and proper operation of the multi-sensing device to accurately detect potential problems of the hydraulic system.

The method 500 continues to block 538 in preparation to record the sensor data into the flash memory 324. In block 538, the method 500 determines whether the flash memory 324 is full. If full, the method 500 continues to block 540 where the warning LED continues to blink rapidly until the sensor data and status is reset. Accordingly, this will ensure that a maintenance technician or other user of the multi-sensing device take appropriate action. If not full, the method 500 proceeds to block 542 where the sensor data is recorded into the flash memory 324. After recording the data, the method 500 loops back to block 524 in the main processing loop 550.

If the sensor data (from the sensing modalities) does not exceed the predetermined alert threshold value as determined in block 544, the method 500 continues to 538. As discussed above, in block 538, the method 500 determines whether the flash memory 324 is full. If full, the method continues to block 540 where the warning LED continues to blink rapidly until the sensor data and status is reset. If not full, the method 500 proceeds to block 542 where the sensor data is recorded to the flash memory 324. After recording the data, the method 500 loops back to block 524 in the main processing loop 550. It is understood that the sensor data that is stored in memory may be time stamped so that a history log of the sensor data may be provided to a maintenance technician during a regularly scheduled maintenance check of the hydraulic system. Further, although both a warning threshold and alert threshold have been disclosed above, it is understood that only a warning threshold, or only an alert threshold, or any number of warning and alert threshold values may be used as well.

Figure 6:
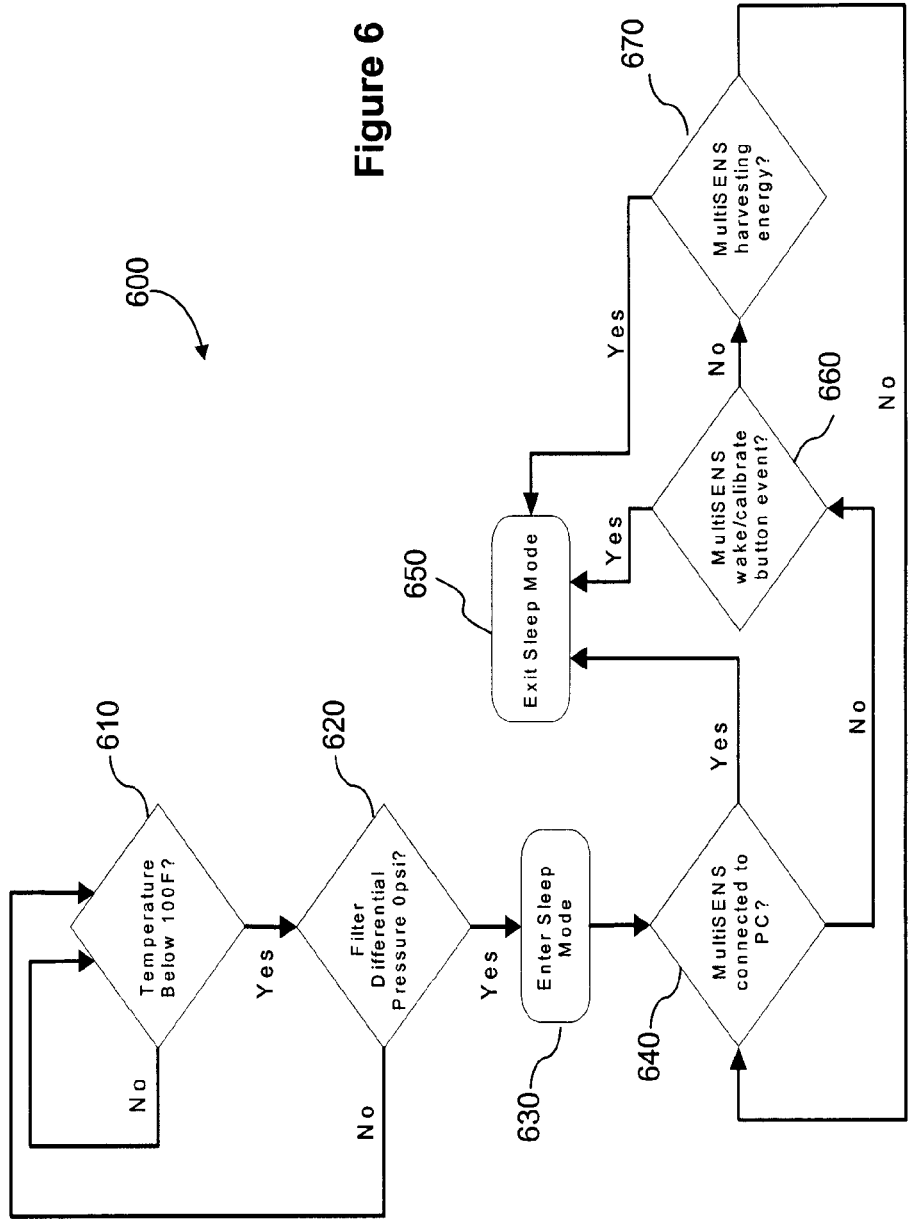
FIG. 6 is a flowchart depicting a method for sleep mode operation of the multi-sensing device of FIG. 3.

Referring to FIG. 6, illustrated is a flowchart of a method 600 for a sleep mode operation of the multi-sensing device 114. The sleep mode operation of the multi-sensing device 114 is implemented when the hydraulic system 100 is in non-use, for example, when the aircraft is not in operation. The method 600 begins in block 610 where it is determined whether the temperature of the hydraulic fluid, such as oil, is below a predetermined threshold value, for example, 100° F. If the oil temperature is not below the predetermined threshold value, the hydraulic system 100 is likely either in operation or has recently shut down. In this case, the multi-sensing device 114 remains in operation and therefore, the method 600 remains at block 610. If the oil temperature is below the predetermined threshold value, the hydraulic system 100 is likely either not in operation or is starting up. Therefore, the multi-sensing device 114 may enter the sleep mode, depending on various other measurements, for example, the filter differential pressure state. In this case, the method 600 proceeds to block 620 where it is determined whether the differential pressure is at or about a predetermined threshold value, for example, 0 psi. If yes, the method 600 proceeds to block 630 where the multi-sensing device 114 enters the sleep mode. In no, the method 600 proceeds to block 610 discussed above.

After entering the sleep mode, the method 600 proceeds to block 640 where it is determined whether the multi-sensing device 114 is connected to a diagnostic or computing device, for example, a PC. If connected, the method 600 proceeds to block 650 where the multi-sensing device 114 exits the sleep mode and returns to normal operation (method 500 of FIG. 5). If not connected, the method 600 proceeds to block 660 where it is determined if the wake/calibrate button 127 has been selected. If selected, the method 600 continues to block 650 where the multi-sensing device 114 exits the sleep mode and returns to normal operation. If not selected, the method 600 continues to block 670 where it is determined whether the multi-sensing device 114 is harvesting energy (e.g., the aircraft's engine is started). If harvesting energy, the method 600 proceeds to block 650 where the multi-sensing device 114 exits the sleep mode and returns to normal operation. If not harvesting energy, the method 600 proceeds to block 640 discussed above.

Figure 7:
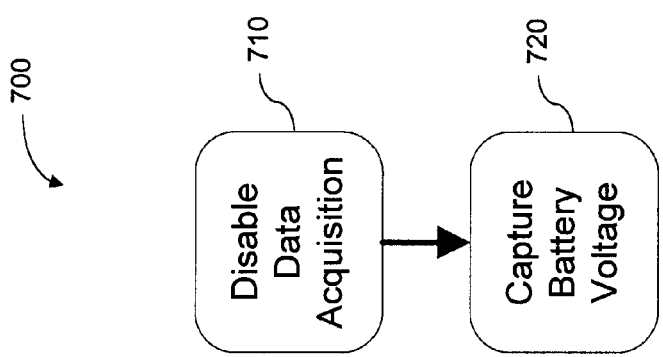
FIG. 7 is a flowchart depicting a method for connecting a computing device to the multi-sensing device of FIG. 3.

Referring to FIG. 7, illustrated is a flowchart of a method 700 for when the multi-sensing device 114 is connected to a diagnostic or computing device, such as a PC. The method 700 begins at block 710 where the main processing loop 550 of the normal operation method 500 is exited, thereby disabling acquisition of sensor and battery information 524. The method 700 continues to block 720 where a battery voltage is captured, which is used to calculate the remaining life of battery 330. During the time when the multi-sensing device 114 is connected to the PC, the PC begins to recharge the battery 330 via the data communication port 328. For example, the data communication port 328 may be configured as a USB port which is capable of supplying power to recharge the battery.

Figure 8:
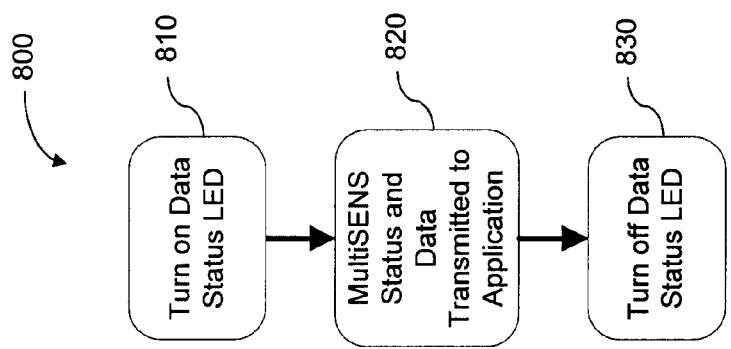
FIG. 8 is a flowchart depicting a method for data extraction from the multi-sensing device of FIG. 3.

Referring to FIG. 8, illustrated is a flowchart of a method 800 for data extraction from the multi-sensing device 114. The method 800 begins executing when a data extraction application is opened while the multi-sensing device 114 is connected to the PC. The data extraction method 800 begins in block 810 where a data status LED (one of the status LEDs 122) is turned on. The data status LED indicates that the communication connection between the multi-sensing device 114 and the data extraction application has been made, and the data extraction application is ready to upload sensor and battery data from multi-sensing device 114. Also, the data status LED indicates to the user that the communication cable between the PC and the multi-sensing device 114 should not be removed while the data status LED is on. The data extraction method 800 continues in block 820 where the status and data of the multi-sensing device 114 is automatically uploaded to the data extraction application. In one embodiment, the data is stored as comma separated values and therefore, the data is exportable to a variety of different data storage and processing applications as is known in the art. After data and status information is transmitted from the multi-sensing device 114 to the data extraction application running on the PC, the method 800 proceeds to block 830. In block 830, the data status LED is turned off, indicating that it is safe to remove the communication cable between the PC and the multi-sensing device 114.

Figure 9:
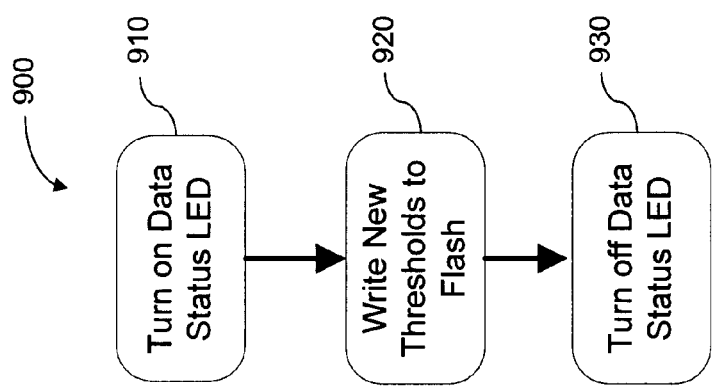
FIG. 9 is a flowchart depicting a method for configuring threshold values for the multi-sensing device of FIG. 3.

Referring to FIG. 9, illustrated is a flowchart of a method 900 for configuring threshold values for the multi-sensing device 114. A user may use a data extraction application to program threshold values for the multi-sensing device 114. For example, the user is able to program new threshold values when either the oil and/or oil filter specifications or oil maintenance guidelines change. Initially, each multi-sensing device 114 may be pre-configured with default threshold values for a system that the multi-sensing device 114 is designed for. For example, if the multi-sensing device 114 is designed for a particular aircraft, the multi-sensing device 114 will include pre-configured threshold values set to default values associated with that particular aircraft. In an alternative embodiment, the multi-sensing device 114 may be initially configured by the user.

The threshold value programming method 900 begins in block 910 when the data status LED turns on to indicate that the data extraction application is prepared to communicate with the multi-sensing device 114. As discussed above when referring to the data extraction routine 800, the data status LED indicates to the user that the communication cable between the PC and the multi-sensing device 114 should not be removed while the data status LED is on. The method 900 proceeds to block 920 where the user enters threshold values into the data extraction application. Also in block 920, the data extraction application transmits the user entered threshold values into the flash memory 324. After threshold values are stored in the stored memory 324, the method 900 proceeds to block 930 where the data status LED is turned off, indicating that it is safe to remove the communication cable between the PC and the multi-sensing device 114.

Figure 10:
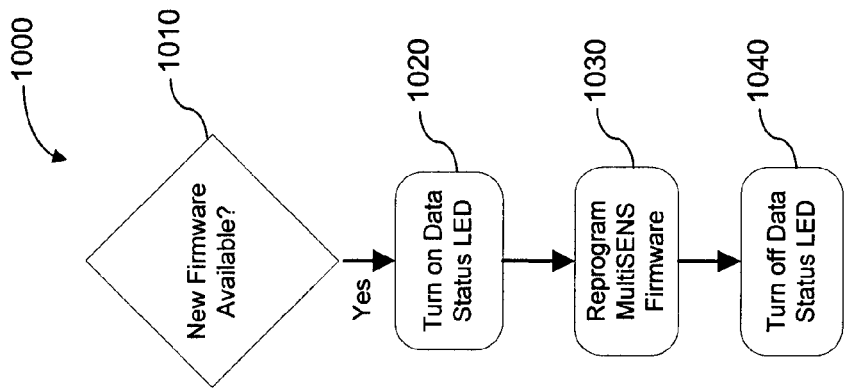
FIG. 10 is a flowchart depicting a method for programming firmware for the multi-sensing device of FIG. 3.

Referring to FIG. 10, illustrated is a flowchart of a method 1000 for programming firmware for the multi-sensing device 114. For example, programming firmware may be accomplished using a data extraction application running on a PC that is coupled to the multi-sensing device 114 via the data communication port 328. The multi-sensing device 114 may initially include pre-programmed firmware. In one embodiment, firmware updates may be made available through files. For example, the files may be e-mailed, posted on servers and websites, or burned to CD-ROMs. In an alternative embodiment, firmware updates may be made available through automatic Internet updates. The firmware programming method 1000 begins in block 1010 where the data extraction application determines whether a new firmware version is available for download to the multi-sensing device 114. For example, the application looks for the new firmware version in a predetermined file storage location on the PC. If the data extraction application determines that there is a new firmware version available for download, the user is prompted accordingly. Alternatively, the user has the option of specifying the location of the new firmware version on the PC.

The method 1000 proceeds to block 1020 if the user answers the prompt by indicating that it is ok to download the new firmware to the multi-sensing device 114. The data status LED turns on, indicating that the data extraction application is prepared to communicate with the multi-sensing device 114. As discussed above, the data status LED indicates to the user that the communication cable between the PC and the multi-sensing device 114 should not be removed while the LED is on. The firmware programming method 1000 proceeds to block 1030 where the data extraction application downloads the firmware to the multi-sensing device 114. Once the firmware download is complete, the method 1000 proceeds to block 1040 where the data status LED is turned off, indicating that it is safe to remove the communication cable between the PC and the multi-sensing device 114.

Figure 11:
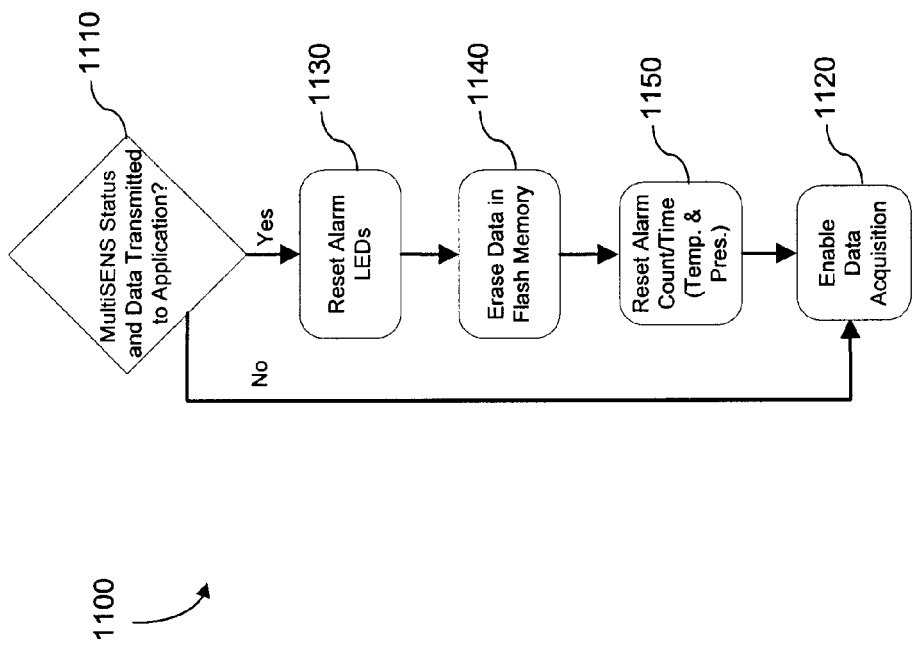
FIG. 11 is a flowchart depicting a method for disconnecting a computing device from the multi-sensing device of FIG. 3.

Referring to FIG. 11, illustrated is a flowchart of a method 1100 for disconnecting the diagnostic or computing device, for example a PC, from the multi-sensing device 114. Once the disconnection is made, the PC ceases charging the battery 330. The disconnecting method 1100 begins in block 1110 where it is determined whether the status and data were successfully uploaded to the data extraction application. For example, if the communication cable between the PC and the multi-sensing device 114 was removed prematurely during the status and data upload process, then the status and data upload was unsuccessful. If unsuccessful, the method 1100 proceeds to block 1120 where the multi-sensing device 114 enters the normal operation main processing loop 550, thereby enabling the acquisition of, for example, sensor and battery information. If the upload was successful, the multi-sensing device 114 will reset its alarm LEDs (in block 1130), erase the sensor and battery data that is stored in the flash memory 324 (in block 1140), and reset the temperature and pressure alarm counters and timers (in block 1150). The method 1100 then proceeds to block 1120 discussed above.

Referring to FIG. 12, illustrated is a flowchart of a method 1200 for operation of a multi-sensing device 114 during a filter element change. For example, the method 1200 assumes that during aircraft operation the hydraulic actuation actions occur unpredictably, and therefore a mechanism is required to determine whether a filter element has been removed from and reinstalled into the filter assembly. However, if it is observed that there are certain hydraulic actuation actions that are guaranteed to be performed while an aircraft is in operation (e.g., enabling the aircraft to either lift or land), and these hydraulic actuation actions cause the fluid flow rate to increase to at least 50% of its maximum, the need to sense filter element removal and reinstallation is obviated.

The method 1200 begins in block 1210 where it is determined whether a filter element has been removed from the filter assembly 108. If no, the method 1200 remains in block 1210. If yes, the method 1200 proceeds to block 1220 where the multi-sensing device 114 ceases its main processing loop 550 (of FIG. 5), if it is not in the sleep mode of operation, and monitors when the filter element is reinstalled into the filter assembly 108. When the filter element has been reinstalled into the filter assembly 108, the multi-sensing device 114 resumes the main processing loop 550, if it is not in the sleep mode of operation. The method 1200 proceeds to block 1230 where it is determined whether the fluid temperature is above the predetermined threshold value of 99° F. In not above, the method 1200 remains in block 1230. If above, the method 1230 proceeds to block 1240 where a differential pressure across the hydraulic filter element is sampled while the fluid temperature remains above the predetermined threshold value of 99° F. The method 1200 proceeds to block 1250 where it is determined whether the differential pressure sample exceeds all previous samples.

For example, in block 1250, the method 1200 determines whether the differential pressure sample exceeds a maximum differential pressure sample that is stored by the multi-sensing device 114 in the flash memory 324. If the sample exceeds the maximum value, the method 1200 continues to block 1260 where the value stored as the maximum differential pressure is replaced by the sample. To that extent, the sample becomes the new maximum differential pressure that is stored in the flash memory 324. On the other hand, if the differential pressure sample does not exceed all previous samples, the method 1200 proceeds to block 1270 to determine whether the oil temperature falls below a predetermined threshold, for example 100° F. If block 1270 determines that the oil temperature does not fall below the predetermined threshold, for example 100° F., the method 1200 loops back to block 1240 where the differential pressure across the hydraulic filter element is sampled. If block 1270 determines that the oil temperature falls below the predetermined threshold, for example 100° F., the method 1200 proceeds to block 1280. In one embodiment, when the oil temperature falls below the predetermined threshold value, for example 100° F., this means the aircraft has performed a single mission since the oil hydraulic filter element was removed and replaced. In block 1280, the routine 1200 checks if the maximum filter differential pressure during the mission was below 25 psi. If block 1280 determines that the pressure was below 25 psi, then this indicates that the hydraulic filer element was successfully changed, and it is safe to reset the data and alarms of the multi-sensing device 114.

Aspects of the present invention may be implemented in software, hardware, firmware, or a combination thereof. The various methods and/or routines disclosed herein, either individually or in combination, may be implemented as a computer program product tangibly embodied in a machine-readable storage device for execution by a processing unit or microcontroller. Various steps of embodiments of the invention may be performed by a computer processor executing a program tangibly embodied on a computer-readable medium to perform functions by operating on input and generating output. Additionally, various steps of embodiments of the invention may provide one or more data structures generated, produced, received, or otherwise implemented on a computer-readable medium, such as a memory.

Although embodiments of the present disclosure have been described in detail, those skilled in the art should understand that they may make various changes, substitutions and alterations herein without departing from the spirit and scope of the present disclosure. For example, although the particular embodiments illustrate specific process steps or procedures, many alternative implementations are possible and may be made by simple design choice. Some process steps may be executed in different order from the specific description herein based on, for example, considerations of function, purpose, conformance to standard, legacy structure, user interface design, and the like. Embodiments disclosed herein have been provided with reference to hydraulic systems using hydraulic oil. However, implementations of embodiments disclosed herein are not limited to any particular type of system or fluid. For example, alternative embodiments can include water filtration and motor oil filtration systems.

What is claimed is:

1. A multi-sensing device for sensing a plurality of characteristics of a fluid flowing through a filter element in a fluid system, the multi-sensing device comprising:
    a first sensor for sensing a temperature of the fluid flowing through the filter element;
    a second sensor for sensing a pressure generated by the fluid flowing through the filter element; and
    an indicator for indicating a condition of the fluid system; and
    a microcontroller operatively coupled to the first and second sensors, the microcontroller executing instructions for:
        receiving temperature data from the first sensor and pressure data from the second sensor;
        if the temperature data does not exceed a first temperature threshold, monitoring subsequent temperature data received from the first sensor until it exceeds the first temperature threshold; and
        if the temperature data exceeds the first temperature threshold:
            determining whether the temperature data exceeds a second temperature threshold and whether the pressure data exceeds a pressure threshold;
            if the temperature data does not exceed the second temperature threshold, evaluating subsequent temperature data received from the first sensor to determine whether it exceeds the second temperature threshold;
            if the temperature data exceeds the second temperature threshold, activating the indicator to indicate that the fluid is in an abnormal condition;
            if pressure data does not exceed the pressure threshold, evaluating subsequent pressure data received from the second sensor to determine whether it exceeds the pressure threshold; and
            if the pressure data exceeds the pressure threshold, activating the indicator to indicate that the filter element is in a condemned condition.

2. The multi-sensing device of claim 1, wherein the pressure threshold corresponds to a pressure generated by the fluid flowing through a dummy filter element, the dummy filter element emulating a filter element that is at a condemned condition.

3. The multi-sensing device of claim 2, wherein the first temperature threshold corresponds to a temperature of the fluid flowing in the fluid system for a period of time, the period of time being sufficiently long to ensure that the fluid system is at an operating condition and wherein the second temperature threshold corresponds to a temperature of the fluid flowing in the fluid system that is overheated.

4. The multi-sensing device of claim 1, wherein the pressure threshold and the first and second temperature thresholds are default threshold values provided by a user of the multi-sensing device.

5. The multi-sensing device of claim 1, wherein the fluid flowing through the filter element in the fluid system includes oil flowing through a hydraulic filter element in a hydraulic system.

6. The multi-sensing device of claim 1, further comprising:
    a battery for supplying power to the components of the multi-sensing device; and
    an energy harvesting module for recharging the battery, the energy harvesting module being configured to harvest vibration energy and translating the vibration energy into electrical energy;
    wherein the multi-sensing device is part of a hydraulic system of an aircraft.

7. The multi-sensing device of claim 1, further comprising a third sensor for sensing a quality of the fluid flowing through the filter element.

8. The multi-sensing device of claim 7, wherein the microcontroller is operatively coupled to the third sensor, the microcontroller executing instructions for:
    receiving fluid quality data from the third sensor;
    determining whether the fluid quality data exceeds a fluid quality threshold;
    if the fluid quality data does not exceed the fluid quality threshold, evaluating subsequent fluid quality data received from the third sensor to determine whether it exceeds the fluid quality threshold; and
    if the fluid quality data exceeds the fluid quality threshold, activating the indicator to indicate that the fluid is contaminated.

9. The multi-sensing device of claim 8, wherein the third sensor includes an optical absorption sensor that senses an optical absorption of the fluid flowing through the filter element; and wherein the optical absorption of the fluid is used to determine the fluid quality, the fluid quality including a metallic particulate content, a viscosity, a water content, an acidity, or an oxidation.

10. The multi-sensing device of claim 7, further comprising memory for storing the temperature data received from the first sensor, the pressure data received from the second sensor, and the fluid quality data received from the third sensor and for storing sensing thresholds.

11. The multi-sensing device of claim 10, further comprising a data port for connecting to a computing device that is capable of executing a data extraction application, the data extraction application being programmed to extract the temperature data, the pressure data, and the fluid quality data stored in the memory, to reprogram instructions for executing by the microcontroller, to calibrate the multi-sensing device, to capture battery voltage from the multi-sensing device, to set the sensing thresholds for the multi-sensing device, to reset the indicators within the multi-sensing device, and to erase stored data in the memory.

12. A method for operating a multi-sensing device that senses a plurality of characteristics of a fluid flowing through a filter element in a fluid system, the method comprising:
acquiring data from a first sensor and a second sensor of the multi-sensing device, the first sensor for sensing a temperature of the fluid flowing through the filter element and the second sensor for sensing a pressure generated by the fluid flowing through the filter element;
if the temperature data does not exceed a first temperature threshold, monitoring subsequent temperature data acquired from the first sensor until it exceeds the first temperature threshold; and
if the temperature data exceeds the first temperature threshold:
determining whether the temperature data exceeds a second temperature threshold and whether the pressure data exceeds a pressure threshold;
if the temperature data does not exceed the second temperature threshold, evaluating subsequent temperature data acquired from the first sensor to determine whether it exceeds the second temperature threshold;
if the temperature data exceeds the second temperature threshold, activating an indicator to indicate that the fluid is in an abnormal condition;
if pressure data does not exceed the pressure threshold, evaluating subsequent pressure data acquired from the second sensor to determine whether it exceeds the pressure threshold; and
if the pressure data exceeds the pressure threshold, activating the indicator to indicate that the filter element is in a condemned condition.

13. The method of claim 12, wherein the pressure threshold corresponds to a pressure generated by the fluid flowing through a dummy filter element, the dummy filter element emulating a filter element that is at a condemned condition.

14. The method of claim 12, wherein the first temperature threshold corresponds to a temperature of the fluid flowing in the fluid system for a period of time, the period of time being sufficiently long to ensure that the fluid system is at an operating condition and wherein the second temperature threshold corresponds to a temperature of the fluid flowing in the fluid system that is overheated.

15. The method of claim 12,
wherein the activating the indicator to indicate that the fluid is in an abnormal condition includes:
setting a temperature status indicator to indicate that the fluid is overheating;
storing the temperature data in a memory of the multi-sensing device; and
updating a count that corresponds to a frequency or a time of the temperature data exceeding the second temperature threshold;
wherein the activating the indicator to indicate that the filter element is in a condemned condition includes:
setting a pressure status indicator to indicate that the fluid element requires changing;
storing the pressure data in the memory of the multi-sensing device; and
updating a count that corresponds to a frequency or a time of the pressure data exceeding the pressure threshold.

16. The method of claim 12, further comprising:
acquiring data from a third sensor of the multi-sensing device, the third sensor for sensing a quality of the fluid flowing through the filter element;
determining whether the fluid quality data exceeds a fluid quality threshold;
if the fluid quality data does not exceed the fluid quality threshold, evaluating subsequent fluid quality data acquired from the third sensor to determine whether it exceeds the fluid quality threshold; and
if the fluid quality data exceeds the fluid quality threshold, activating the indicator to indicate that the fluid is contaminated.

17. The method of claim 16, wherein the third sensor includes an optical absorption sensor that senses an optical absorption of the fluid flowing through the filter element; and
wherein the optical absorption of the fluid is used to determine the fluid quality, the fluid quality including a metallic particulate content, a viscosity, a water content, an acidity, or an oxidation.

18. The method of claim 16, wherein the acquiring the data from the first, second, and third sensors includes:
receiving a number of sample readings from each of the first, second, and third sensors over a period of time; and
averaging the number of sample readings from each of the first, second, and third sensors to generate the temperature data, pressure data, and fluid quality data.

19. The method of claim 12, further comprising calibrating the multi-sensing device that includes:
installing a dummy filter element in the fluid system, the dummy filter element emulating a filter element that is in the condemned condition;
performing a repeatable action that causes a differential pressure to be generated across the dummy filter element by fluid flowing, the repeatable action corresponding to an actuation action in a hydraulic system; and
measuring and storing the differential pressure as the pressure threshold in a memory of the multi-sensing device.

20. The method of claim 19, further comprising performing a scheduled maintenance check of the hydraulic system that includes:
performing the same repeatable action that was performed during the calibration to enhance a reliability of the multi-sensing device in determining when the filter element requires changing;
measuring a differential pressure that is generated across the filter element in response to the performing the same repeatable action; and
comparing the measured differential pressure to the pressure threshold to determine whether the filter element is in the condemned condition.

21. A fluid system comprising:
a filter assembly having an inlet port and an outlet port, the filter assembly including a filter element for filtering a fluid flowing in the inlet port and out the outlet port; and
a multi-sensing device operatively coupled to the filter assembly for sensing a plurality of characteristics of the fluid flowing through the filter element of the filter assembly, the multi-sensing device including:
  a first sensor for sensing a temperature of the fluid;
  a second sensor for sensing a pressure generated by the fluid flow;
  an indicator for indicating a condition of the fluid system;
  memory for storing data; and
  a microcontroller having instructions for:
    acquiring temperature data from the first sensor and pressure data from the second sensor; and
    if the temperature data exceeds a first temperature threshold:
      determining whether the temperature data exceeds a second temperature threshold and whether the pressure data exceeds a pressure threshold;
      if the temperature data exceeds the second temperature threshold, activating the indicator to indicate that the fluid is in an abnormal condition and storing the temperature data in the memory; and
      if the pressure data exceeds the pressure threshold, activating the indicator to indicate that the filter element is in a condemned condition and storing the pressure data in memory.

22. The fluid system of claim 21,
wherein the multi-sensing device further includes a third sensor for sensing a quality of the fluid; and
wherein the microcontroller further includes instructions for:
  acquiring fluid quality data from the third sensor;
  determining whether the fluid quality data exceeds a fluid quality threshold; and
  if the fluid quality data exceeds the fluid quality threshold, activating the indicator to indicate that the fluid is contaminated and storing the fluid quality data in the memory.

23. The fluid system of claim 22, wherein the third sensor includes an optical absorption sensor that senses an optical absorption of the fluid flowing through the filter element; and
wherein the optical absorption of the fluid is used to determine the fluid quality, the fluid quality including a metallic particulate content, a viscosity, a water content, an acidity, or an oxidation.

24. The fluid system of claim 22, wherein the indicator includes:
  a temperature status indicator for indicating that the fluid is overheating;
  a pressure status indicator for indicating that the fluid element requires changing; and
  a fluid quality indicator for indicating that the fluid requires changing.

25. The fluid system of claim 21, wherein the fluid system is a hydraulic system and the fluid is oil.

* * * * *